United States Patent
Shohami et al.

(10) Patent No.: US 6,545,041 B2
(45) Date of Patent: *Apr. 8, 2003

(54) TUMOR NECROSIS FACTOR ALPHA (TNF-α) INHIBITING PHARMACEUTICALS

(75) Inventors: Esther Shohami, Jerusalem (IL); Ruth Gallily, Jerusalem (IL); Raphael Mechoulam, Jerusalem (IL)

(73) Assignee: Yessum Research Development Co. of the Hebrew University of Jerusalem, Jerusalem (IL)

( * ) Notice: Subject to any disclaimer, the term of this patent is extended or adjusted under 35 U.S.C. 154(b) by 0 days.

This patent is subject to a terminal disclaimer.

(21) Appl. No.: 09/971,821

(22) Filed: Oct. 4, 2001

(65) Prior Publication Data

US 2002/0049245 A1 Apr. 25, 2002

Related U.S. Application Data (63) Continuation of application No. 09/318,774, filed on May 26, 1999, now Pat. No. 6,331,560, which is a continuation of application No. 08/952,660, filed as application No. PCT/IL96/00108 on Sep. 10, 1996, now Pat. No. 5,932,610.

(30) Foreign Application Priority Data

Sep. 11, 1995 (IL) ................................................. 115245

(51) Int. Cl.$^7$ ................................................. A61K 31/35
(52) U.S. Cl. ...................................... 514/454; 514/455
(58) Field of Search ................................. 514/454, 455

(56) References Cited

U.S. PATENT DOCUMENTS

| 5,284,867 A | 2/1994 | Kloog et al. ................. 514/454 |
| 5,338,753 A | 8/1994 | Burstein et al. ............. 514/454 |

OTHER PUBLICATIONS

Zheng et al., 118CA:116543.
Watzl et al. 116CA:76203.

*Primary Examiner*—Russell Travers
(74) *Attorney, Agent, or Firm*—Winston & Strawn (57) ABSTRACT

Pharmaceutical compositions are described for preventing TNF toxicity, comprising as active ingredient the stereospecific (+) enantiomer, having (3S,4S) configuration of $\Delta^6$ tetrahydrocannabinol type compounds. The compositions are particularly effective in alleviating and even preventing neurotoxicity due to elevated levels of TNF, including septic shock, cachexia and trauma. They are also effective in the treatment of certain chronic degenerative diseases characterized by TNF production, including autoimmune diseases such as AIDS.

18 Claims, 7 Drawing Sheets

TUMOR NECROSIS FACTOR ALPHA (TNF-α) INHIBITING PHARMACEUTICALS

CROSS-REFERENCE TO RELATED APPLICATIONS

This application is a continuation of application Ser. No. 09/318,774, filed May 26, 1999, now U.S. Pat. No. 6,331,560 which is a continuation of application Ser. No. 08/952,660 filed Nov. 17, 1997, now U.S. Pat. No. 5,932,610 which is a 371 of PCT/IL96/00108 filed Sep. 10, 1996.

FIELD OF THE INVENTION

The present invention relates to the use of pharmaceutical compositions for inhibiting the production or blocking the action of Tumor Necrosis Factor α (TNF-α), and for preventing or alleviating diseases and conditions associated with this cytokine, such as septic shock or cachexia. Said pharmaceutical compositions comprise as their active ingredient the stereospecific (+) enantiomers, having (3S,4S) configuration, of $\Delta^6$-tetrahydrocannabinol (THC) type compounds of general formula (I), as defined hereinbelow.

(I)

BACKGROUND OF THE INVENTION

Tumor necrosis factor alpha (TNF-α) is a pleiotropic cytokine, which has been implicated in inflammatory and immunological responses, as well as in pathogenesis of endotoxic and septic shock (reviewed by Tracey and Cerami, Ann. Rev. Med. 45, 491–503, 1994; Glauser et al. Clin. Infect Dis. 18, suppl. 2, 205–216, 1994). TNF is one of several cytokines released mainly by mononuclear phagocytic cells in response to various stimuli. Though the role of cytokines in pathophysiological states has not been fully elucidated, it appears that TNF-α is a major mediator in the cascade of injury and morbidity.

Among the serious disease states related to the production of TNF-α, a partial list includes the following: septic shock; endotoxic shock; cachexia syndromes associated with bacterial infections (e.g., tuberculosis, meningitis), viral infections (e.g., AIDS), parasite infections (e.g., malaria), and neoplastic disease; autoimmune disease, including some forms of arthritis (especially rheumatoid and degenerative forms); and adverse effects associated with treatment for the prevention of graft rejection.

Septic shock is an often lethal syndrome associated with the massive release of host cytokines due to stimuli present on, or released by, invasive micro-organisms. These invasive stimuli induce polyclonal stimulation of the infected host immune system, and include both lipopolysaccharide (LPS), an endotoxin that stimulates B-cells and macrophages, and superantigens which are exotoxins that stimulate T-cells.

Septic shock has been recognized generally as a consequence of gram-negative bacterial infection, but it is now clear that it can also result from infection with gram positive micro-organisms and probably also by fungi, viruses and parasites. The microorganism itself, its components or products trigger the host cells, especially the macrophages, to release inflammatory mediators such as TNF-α, thereby initiating a cascade of events leading to cachexia, sepsis syndrome and septic shock. TNF-α is a major mediator initiating septic shock, and therefore stands out as a potential therapeutic target (Lynn and Cohen, Clin. Infect. Dis. 20, 143–158, 1995).

Despite vast improvements in intensive care and antibiotic therapy, septic shock remains associated with a very high rate of mortality (30 to 90%). The poor prognosis for this syndrome is due to the fact that this severe complication of infection results in multiple organ failure, even when the actual infection itself is successfully treated. It is, therefore, apparent that effective therapies for this syndrome are an unmet medical need.

Various therapies have been suggested for the treatment of septic shock syndrome, but as yet none of these has proven to be clinically efficacious. Antibodies against TNF-α prevent the detrimental effects of superantigen (Miethke et al., J. Exp. Med. 175, 91–98, 1992) or LPS (Beutler et al., Science 229, 869–871, 1985). The use of anti-TNF antibodies to treat septic shock is disclosed for example in WO 92/16553 (Centocor Inc.). WO 92/01472 (Celltech Ltd.) discloses a multivalent immunoglobulin used to treat diseases associated with elevated cytokine levels. Various cytokines that inhibit TNF secretion can also reduce the toxicity of LPS action (Tzung et al., Eur. J. Immunol. 22, 3097–3101, 1992; Gerard et al., J. Exp. Med. 177, 547–550, 1993).

Soluble forms of the TNF binding protein (TBP) (Nophar et al. EMBO J., 9, 3269–3278, 1990) may prevent the action of TNF by preventing binding to its receptors.

Specific classes of compounds have been suggested for the treatment of diseases associated with elevated TNF or other inflammatory mediators, as disclosed for example in WO 95/11014 (Searle & Co.); WO 95/09627, WO 95/09624 and WO 95/09623 (Smith-Kline Beecham Corp.); WO 95/09619 (Wellcome Found.); WO 95/03051 (Pharmacia AB); WO 95/01980 (Pfizer Inc.); EP 629401 (Bayer AG); WO 93/14082 (SmithKline Beecham Corp.); and WO 89/05145 (Hoechst Roussel Pharm Inc.).

None of these disclosures is relevant to the present invention, which deals with a class of compounds developed as non-psychotropic analogs of tetra-hydrocannabinol (THC), the active ingredient of marijuana. Some of the compounds of general formula (I) are disclosed in U.S. Pat. Nos. 4,179,517 and 4,876,276 and 5,284,867. As disclosed in said U.S. patents, these essentially pure synthetic (+)-(3S, 4S)-THC derivatives and analogues are devoid of any undesired cannabimimetic psychotropic side-effects. These known compounds have been described as having analgesic, antiemetic, antiglaucoma and neuroprotective activity.

According to the present invention, it is now disclosed that the said known compounds, as well as some novel compounds, in addition to having said analgesic, antiemetic, neuroprotective and anti-glaucoma activity, are unexpectedly also effective against the diseases and conditions mentioned above, by virtue of their ability to block the production or action of TNF-α.

SUMMARY OF THE INVENTION

The present invention provides pharmaceutical compositions for reducing and even preventing morbidity and mortality associated with the production of TNF-α, or other cytokines. The present compositions are also effective in alleviating other cytokine induced damage including the wasting or cachexia associated with AIDS, tuberculosis, neoplasia or trauma, and may prevent or ameliorate other disease states associated with the production of cytokines, including malaria and parasitic infections.

The compositions of the present invention are also effective in the treatment of certain chronic degenerative diseases including arthritis and other autoimmune afflictions which are characterized by production of TNF-α. In this connection, the compositions of the present invention are contemplated as therapeutically effective in the treatment of multiple sclerosis. In addition, the present compositions can be administered to a patient who exhibits the symptoms associated with cachexia due to acquired immune deficiency syndrome, neoplasia, trauma or other wasting syndromes, as well as to those having other autoimmune diseases.

The present invention relates to pharmaceutical compositions for the purposes set out above, in which the active ingredient is a compound of the general formula I:

(I)

having the (3S,4S) configuration and being essentially free of the (3R,4R) enantiomer, wherein A - - - B indicates an optional 1(2) or 6(1) double bond,
R is
(a) —Q wherein Q is a heterocyclic moiety having a labile hydrogen atom so that said moiety acts as a carboxylic acid analogue,
(b) —R'X wherein R' is $C_1$–$C_5$ alkyl and X is halogen, —OR'' wherein R'' is hydrogen, $C_1$–$C_5$ alkyl, or —OC(O)R''' wherein R''' is hydrogen or $C_1$–$C_5$ alkyl,
(c) —R'N(R'')$_2$ wherein R' is $C_1$–$C_5$ alkyl and each R'', which may be the same or different, is hydrogen or $C_1$–$C_5$ alkyl optionally containing a terminal —OR''' or —OC(O)R''' moiety wherein R''' is hydrogen or $C_1$–$C_5$ alkyl,
(d) —R' wherein R' is $C_2$–$C_5$ alkyl,
(e) —R'OR''' wherein R' is $C_1$–$C_5$ alkyl and R''' is hydrogen or $C_1$–$C_5$ alkyl, or
(f) —R'—C(O)OR''', wherein R''' may be absent and R' and R''' are as defined above;
G is (a) halogen, (b) $C_1$–$C_5$ alkyl, or (c) —OR$_1$ wherein R$_1$ is (a') —R'', wherein R'' is hydrogen or $C_1$–$C_5$ alkyl optionally containing a terminal —OR''' or —OC(O)R''' moiety wherein R''' is hydrogen or $C_1$–$C_5$ alkyl, or (b') —C(O)R''' wherein R''' is as previously defined; and
R$_2$ is (a) $C_1$–$C_{12}$ alkyl, (b) —OR'''', in which R'''' is a straight chain or branched $C_2$–$C_9$ alkyl which may be substituted at the terminal carbon atom by a phenyl group, or (c) —(CH$_2$)$_n$OR''' wherein n is an integer of 1 to 7 and R''' is hydrogen or $C_1$–$C_5$ alkyl.

In a currently preferred group of compounds, R$^2$ designates a 1,1-dimethylalkyl radical or a 1,2-dimethylalkyl radical with a total of at least 7 carbon atoms. Also preferred are precursors of such compounds. Particularly preferred compounds are those wherein R$^2$ is 1,1-dimethylheptyl or 1,2-dimethylheptyl. It is these embodiments of R$^2$ that are found in THC and its analogues. However, for the cytokine-inhibiting activity that characterizes the present invention, it is believed that any lower or mid-range alkyl substituent will be suitable at this position.

The compositions of the present invention are particularly effective in alleviating and even preventing morbidity and mortality associated with the production of TNF-α, or other cytokines. Methods are provided for treatment of diseases associated with the production of TNF-α by administering to a patient in need thereof a composition comprising as active ingredient a therapeutically effective amount of a compound of general formula I.

BRIEF DESCRIPTION OF THE DRAWINGS

FIG. 1 shows the attenuating effect of HU-211 on TNF activity (FIG. 1A) and in reducing TNF levels in the serum of mice (FIG. 1B) following the administration of endotoxin, LPS.

FIG. 2 shows the protective effect of HU-211 in preventing mortality of mice following the administration of LPS alone, (FIG. 2A) or following its administration to galactose-amine-sensitized mice (FIG. 2B).

FIG. 3 shows the beneficial effect of HU-211 on blood pressure (FIG. 3a) and on the hematocrit (FIG. 3b) of rats, following LPS administration.

FIG. 4 shows the beneficial effect of HU-211 on the clinical outcome (A), on TNF levels (B) and on cerebral edema (C) in rat brain after closed head injury. The effects of pentoxifylline are shown for comparison (B,C).

DETAILED DESCRIPTION OF THE PREFERRED EMBODIMENTS

The present invention provides pharmaceutical compositions for reducing and even preventing morbidity and mortality associated with the production of TNF-α, or other cytokines. The present compositions are also effective in alleviating other cytokine induced damage including wasting or cachexia associated with AIDS, tuberculosis, neoplasia or trauma, and may prevent or ameliorate other disease states associated with the production of cytokines, including parasitic infections.

The compositions of the present invention may also be effective in the treatment of certain chronic degenerative diseases including arthritis and other autoimmune afflictions which are characterized by production of TNF-α. In this connection, the compositions of the present invention are contemplated as therapeutically effective in the treatment of multiple sclerosis.

The present invention relates to pharmaceutical compositions for the purposes set out above, in which the active ingredient is a compound of the general formula (I):

(I)

having the (3S,4S) configuration and being essentially free of the (3R,4R) enantiomer, wherein A - - - B indicates an optional 1(2) or 6(1) double bond,
R is
(a) —Q wherein Q is a heterocyclic moiety having a labile hydrogen atom so that said moiety acts as a carboxylic acid analogue,
(b) —R'X wherein R' is $C_1$–$C_5$ alkyl and X is halogen, —OR'' wherein R'' is hydrogen, $C_1$–$C_5$ alkyl, or —OC(O)R''' wherein R''' is hydrogen or $C_1$–$C_5$ alkyl,
(c) —R'N(R'')$_2$ wherein R' is $C_1$–$C_5$ alkyl and each R'', which may be the same or different, is hydrogen or $C_1$–$C_5$ alkyl optionally containing a terminal —OR''' or —OC(O)R''' moiety wherein R''' is hydrogen or $C_1$–$C_5$ alkyl, (d) —R' wherein R' is $C_2$–$C_5$ alkyl,
(e) —R'OR''' wherein R' is $C_1$–$C_5$ alkyl and R''' is hydrogen or $C_1$–$C_5$ alkyl, or
(f) —R'—C(O)OR''', wherein R' may be absent and R' and R''' are as defined above;
G is (a) halogen, (b) $C_1$–$C_5$ alkyl, or (c) —OR$_1$ wherein R$_1$ is (a') —R'', wherein R'' is hydrogen or $C_1$–$C_5$ alkyl optionally containing a terminal —OR''' or —OC(O)R''' moiety wherein R''' is hydrogen or $C_1$–$C_5$ alkyl, or (b') —C(O)R''' wherein R''' is as previously defined; and
R$_2$ is (a) $C_1$–$C_{12}$ alkyl, (b) —OR'''', in which R'''' is a straight chain or branched $C_2$–$C_9$ alkyl which may be substituted at the terminal carbon atom by a phenyl group, or (c) —(CH$_2$)$_n$OR''' wherein n is an integer of 1 to 7 and R''' is hydrogen or $C_1$–$C_5$ alkyl.

In a currently preferred group of compounds, R$^2$ designates a 1,1-dimethylalkyl radical or a 1,2-dimethylalkyl radical with a total of at least 7 carbon atoms. Also preferred are precursors of such compounds. Particularly preferred compounds are those wherein R$^2$ is 1,1-dimethylheptyl or 1,2-dimethylheptyl. It is these embodiments of R$^2$ that are found in THC and its analogues. However, for the cytokine-inhibiting activity that characterizes the present invention, it is believed that any lower or mid-range alkyl substituent will be suitable at this position.

A preferred compound, with which many of the physiological experiments have been carried out, is the compound which may be referred to as the (+)-(3S,4S)-1,1-dimethylheptyl homologue of 7-hydroxy-$\Delta^6$-tetrahydrocannabinol. Said compound is designated hereinafter as HU-211, or by the trivial chemical name dexanabinol.

It is stressed that all the compounds are of the (+)-(3S,4S) configuration, essentially free of the (−)-(3R,4R) enantiomer, the latter known to possess the undesired psychotropic side-effects. Thus, for example, the enantiomers of the synthetic cannabinoid 7-hydroxy-$\Delta^6$-tetrahydrocannabinol 1,1-dimethylheptyl homologue, have been described [Mechoulam, R., et al., *Tetrahedron:Asymmetry* 1: 315–319, 1990; Mechoulam, R. et al., *Experientia* 44: 762–764, 1988]. The (−)-(3R,4R) enantiomer, herein designated HU-210, is a highly potent cannabimimetic compound (nearly 100 times more active than $\Delta$-1-tetrahydrocannabinol, the active component of hashish). The (+)-(3S,4S) enantiomer, herein designated HU-211, while known to be active as a neuroprotective agent, an analgesic and as an anti-emetic, is inactive as a cannabimimetic even at doses several thousand times higher than the ED$_{50}$ of HU-210 (Mechoulam, R. et al., *Experientia* 44: 762–764, 1988).

Another family of stereospecific compounds that falls within the scope of the present invention is the family of analogs comprising (3S,4S)-delta-6-tetrahydrocannabinol-7-oic acids and derivatives thereof, in which R in formula 1 bears a carboxylic acid, as exemplified by the prototype compound HU-245. HU-245 and its analogs are disclosed in international patent application WO 93/05031 which is hereby incorporated in its entirety by reference.

As mentioned above, the compounds of the general formula (I) as defined herein are substantially devoid of cannabimimetic central nervous system activity.

Pharmacology

The novel compositions contain in addition to the active ingredient conventional pharmaceutically acceptable carriers, diluents and the like. Solid compositions for oral administration such as tablets, pills, capsules or the like may be prepared by mixing the active ingredient with conventional, pharmaceutically acceptable ingredients such as corn starch, lactose, sucrose, sorbitol, talc, stearic acid, magnesium stearate, dicalcium phosphate and gums with pharmaceutically acceptable diluents. The tablets or pills can be coated or otherwise compounded with pharmaceutically acceptable materials known in the art to provide a dosage form affording prolonged action or sustained release. Other solid compositions can be prepared as suppositories, for rectal administration. Liquid forms may be prepared for oral administration or for injection, the term including subcutaneous, transdermal, intravenous, intrathecal, and other parenteral routes of administration. The liquid compositions include aqueous solutions, with or without organic cosolvents, aqueous or oil suspensions, flavored emulsions with edible oils, as well as elixirs and similar pharmaceutical vehicles. In addition, the compositions of the present invention may be formed as aerosols, for intranasal and like administration.

The active dose for humans is generally in the range of from 0.05 mg to about 50 mg per kg body weight, in a regimen of 1–4 times a day, or by constant infusion. However, administration every two days or even less frequently may also be possible, as the drug has a rather prolonged action. The preferred range of dosage is from 0.1 mg to about 25 mg per kg body weight. However, it is evident to one skilled in the art that dosages would be determined by the attending physician, according to the disease to be treated, method of administration, patient's age, weight, contraindications and the like.

All the compounds defined above are inhibitors of tumor necrosis factor alpha (TNF-α), and can be used as active ingredients of pharmaceutical compositions for treatment of one, or simultaneously several, symptoms of the disorders defined above. The effective dosages are essentially similar, and the more pronounced effect is that of inhibition of TNF-α production, in addition to the known characteristics of these compounds. However, it is important to note that the compounds and compositions of the present invention may exert their beneficial effects by other mechanisms, and specifically may prevent the action of TNF-α indirectly via their induction of and/or action on other cytokines. For example, the compositions of the present invention can prevent, or at least alleviate, IL-1 and IL-6 production, as well as poisoning caused by nitric oxide.

The compounds of the present invention are administered for the above defined purposes in conventional pharmaceutical forms, with the required solvents, diluents, excipients, etc. to produce a physiologically acceptable formulation. They can be administered by any of the conventional routes of administration. The required dose for humans ranges from 0.005 mg/kg to about 50 mg/kg per unit dosage form. The most preferred unit dose range is from about 0.1 mg/kg to about 20 mg/kg body weight.

It will be appreciated that the most appropriate administration of the pharmaceutical compositions of the present invention will depend on the type of injury or disease being treated. Thus, the treatment of septic shock will necessitate systemic administration of the drug as rapidly as possible after diagnosis of the condition. On the other hand, diminution or prophylaxis of chronic degenerative damage will necessitate a sustained dosage regimen.

HU-211 conveys significant protection in different models of septic shock associated with bacterial infection or in models of traumatic shock.

The invention also relates to methods of treatment of the various pathological conditions described above, by administering to a patient a therapeutically effective amount of the compositions of the present invention. The term administration as used herein encompasses oral, parenteral, intravenous, intramuscular, subcutaneous, transdermal, intrathecal, rectal and intranasal administration.

It was shown previously that the pharmacological profile of HU-211, and some other compounds constituting the active ingredients of the present compositions, includes the induction of stereotypy and locomotor hyperactivity (Feigenbaum et al., 1989 ibid.). These effects were observed at doses far exceeding those contemplated for use in connection with repression of cytokines. Indeed Phase I clinical trials of HU-211, administered intravenously to healthy human volunteers showed no evidence of toxicity or psychoactivity of these compounds within the dose ranges contemplated for use in humans.

Test Systems

Evaluation of the therapeutic effects of HU-211 and its analogs has now been carried out in a series of experimental systems of increasing sophistication to support the utility of these drugs as inhibitors of TNF-α.

The TNF inhibitory and/or protective effects have been evaluated both in vitro and in vivo. These beneficial protective effects have been corroborated in the following systems:

(a) Lowering TNF Production in Rat Brain After LPS Administration:
The administration of LPS to experimental animals triggers the biosynthesis of large quantities of TNF. After binding to its receptor, TNF induces a wide variety of cellular responses, which are implicated in the pathogenesis of septic shock.
Rats injected with LPS into their brain (intra-cerebral-ventricular, icv, injection) serve as a model for endotoxic shock, and the ability of compounds to inhibit the production in the brain of any of the mediators (e.g. TNF, interleukins) which are activated in response to LPS is a measure of their potency as anti-endotoxic agents.

(b) Reduced TNF Levels in the Serum of Mice After LPS Administration:
An early response to LPS administration is the elevation of serum levels of TNF, which peaks at 1.5–2 hr after LPS administration. Mice treated with LPS serve as a model for the effect of drugs on reducing TNF levels under these conditions.

(c) Reduced LPS-Induced Hypotension in the Rat:
A prominent manifestation of endotoxemia is hypotension, and the effect of a drug on mean arterial blood pressure (MABP) indicates its potency as an anti-endotoxic shock agent. The protective effect of a test compound is evaluated in rats treated with LPS, in which the blood pressure and other vital signs are monitored up to 4 hrs after induction of endotoxemia.

(d) Improved Clinical Outcome After Closed Head Injury in Rats:
Closed head injury is associated with high mortality and morbidity. It induces edema formation, blood-brain-barrier (BBB) disruption, neuronal cell death and impairment of motor and cognitive functions. Animals subjected to head trauma in a controlled fashion serve as models in which to test drugs of therapeutic potential. Test compounds can be evaluated both for improved clinical outcome and for reduction of edema induced by closed head injury. The ability of compounds to reduce the severity of neurological symptoms and to reduce brain edema is considered a measure of their potency in reducing brain damage.

(e) Improved Clinical Outcome in Experimental Autoimmune Diseases in Rats:
Autoimmune diseases are associated with elevated levels of TNF. The models which are most conveniently studied are experimental allergic encephalomyelitis (EAE) and experimental autoimmune arthritis in rodents. EAE is an autoimmune neurological disease elicited by sensitization of the animals to myelin basic protein from the central nervous system, which is also known as basic encephalitogenic protein. EAE is considered by many to represent a model of the human disease multiple sclerosis. Experimental autoimmune arthritis is induced in animals by immunization with collagen in complete Freund's adjuvant. The ability of compounds of the general formula I to prevent or attenuate the clinical symptoms of these autoimmune diseases was tested.

Each of these systems represents an aspect of endotoxin toxicity which is amenable to intervention by pharmaceutical agents. It is likely that the compounds of the present invention exert their demonstrated protective effects by virtue of their ability to prevent the production of TNF-α. Nevertheless, it cannot be ruled out that their activity is mediated by other cytokines or additional mechanisms.

The prototype drug used for evaluation of prevention of release of TNF-α is the compound pentoxifylline, a known inhibitor of TNF release, and we have evaluated the similarities and differences between the biological activities of this compound and HU-211, as summarized in Table 1.

This evaluation clearly supports the concept that HU-211 is not acting solely by blocking the release of tumor necrosis factor. Rather the therapeutic effects of HU-211 may be attributable to additional mechanisms including suppression of TNF production or blockade of TNF action, among others.

Importantly, it has been shown that the activity of these compounds is stereospecific and that the psychotropic (−) compounds are of lower activity or even not active in these systems. Thus, HU-210 is not effective in preventing the action of TNF in vivo. This supports the concept that the suppression of TNF is not the known immunomodulatory activity, such as has been described for a variety of psycho-active enantiomers of cannabinoids and analogs (Lynn and Herkenham, J. Pharmacol. and Exp. Ther., 286, 1612–1623, 1993). Even if the (−) compounds were as effective as the (+)

compounds of the present invention the severe psychotropic activity of the former would make their medical use prohibitive.

Compounds

Experiments have shown that the (+)-(3S,4S) stereoisomer of the compound of formula I wherein A - - - B designates a 6(1) double bond, R is methyl, G is OH, and $R^2$ is 1,1-dimethylheptyl and the compound of formula I wherein A - - - B designates a 1(2) double bond, R is methyl, G is OH, and $R^2$ is 1,1-dimethylheptyl, both said compounds being essentially free of the (−)-(3R,4R) enantiomer, have practically the same activity as that of the compound designated HU-211. The former compound is designated compound Vb in U.S. Pat. No. 4,179,517; the latter compound is compound XIb therein.

In addition it has been found that some novel compounds of general formula (I), wherein R designates $CH_2OR'$ and R' designates an acyl group also have the desired activity. These novel compounds may be prepared, for example, by esterification of compounds of general formula (I) wherein R designates $CH_2OH$ and G is OH, under conditions which favor the formation of the desired monoesters with relatively high yield.

Among the novel compounds tested, monoesters including nicotinate, succinate and maleate are preferred. Most preferred compounds include the glycinate ester and N-substituted glycinate ester salts, such as the trimethyl- and triethylammonium acetate derivatives of HU-211. These novel compounds have the added advantage of being soluble in some aqueous solutions, whereas the parent compounds are extremely hydrophobic.

The highly lipophilic character of HU-211 enables the compound to enter the central nervous system, as it readily passes the blood-brain barrier. However, the high lipid solubility is also associated with very poor solubility in water. This makes the development of formulations suitable for intravenous administration of HU-211 difficult, hampering its clinical application. Water-soluble derivatives of HU-211 designed to readily release the drug by hydrolysis following i.v. administration might overcome this problem and will be used as prodrugs. On the other hand, if the obtained derivatives are hydrolytically stable but possess intrinsic biological activity they could be used as easy-to-formulate analogs (congeners) possessing significant NMDA antagonist activity.

The novel derivatives are obtained by the attachment of polar or permanent charge bearing groups to the allylic (C-7) or phenolic (C-3') hydroxylic functionalities of HU-211, the two sites suitable for reversible structural modification, through a carboxylic ester or phosphate linkage.

EXAMPLES

TNF is released by mononuclear phagocytes and from astrocytes in response to infection or endotoxin. It has been implied that TNF mediates the lethal effect of endotoxic shock. In the next examples we describe the use of LPS as a model for endotoxic shock in rats and mice and the effect of HU-211 on a) TNF production in response to LPS challenge, and b) on some physiological manifestations of LPS toxicity. The following examples are intended to illustrate the present invention and these are to be construed in a non-limitative manner.

Physiological Example 1

The Effect of HU-211 on Rat Brain Production of TNF After LPS Administration.

The biological activity (bioassay) of TNF in extracts prepared from rat brains following intracerebral injection of LPS was assessed. LPS administration triggers the production of TNF and the effect of HU-211, and other analogs administered 15 min before LPS was evaluated 2 hr later. HU-211 and HU-245 significantly attenuated the increase in biological activity of TNF in homogenates prepared from brains of LPS treated rats.

Experimental Procedure:

LPS (50 ug, dissolved in 20 ul saline) was injected into the cerebral lateral ventricle and within 5 min of injection, HU-211 7.5 mg/kg iv was administered. Two hours later, the rats were decapitated, their brains removed, and segments of the cortical tissue taken for cytokines extraction in DMEM (Dulbecco's modified Eagle's medium), and analysis of biological activity using bioassay (Shohami et. al., J. Cereb. Blood Flow Metabol., 14, 615–619, 1994).

Results:

The activity of TNF (expressed as $S_{50}$, see Shohami et al. ibid., for details) in control (LPS) treated rats was 407±172 whereas in the HU-211-treated rats it reached only 43±21. These results clearly demonstrate that HU-211 reduced the biological activity of TNF in the brain homogenates. In contrast, the (−) enantiomer, which is denoted HU-210 did not affect TNF levels when administered to rats under similar conditions ($S_{50}$=660±267 in LPS treated rats vs. 783±410 in the LPS+HU-210 treated rats). This establishes the stereospecificty of the effect of the non-psychotropic (+) enantiomer.

The evaluation of analogs was extended to include rats treated with HU-245 at a dose of 5 mg/kg. Upon bioassay of TNF, these animals were found to have a $S_{50}$ of 89±36, vs. 448±146 found for the LPS control animals.

The results obtained in the bioassay of TNF activity were confirmed by ELISA.

Conclusion:

One of the typical host responses to LPS is increased production and activity of TNF, which is implicated in the pathophysiology of endotoxic shock. The present results demonstrate that HU-211, but not its enantiomer HU-210, may reduce this local response (LPS was injected directly into the brain, where the TNF production was assessed). HU-245 treated animals also had a significantly lowered level of TNF activity.

Physiological Example 2

The Effect of HU-211 on Serum Levels and Biological Activity of TNF in LPS Treated Mice.

The following experiment was designed to assess the peripheral effect of HU-211 on serum levels of TNF in LPS treated mice.

Serum levels of TNF peak within 1.5 hr following LPS administration, and at this time point, we assessed both TNF activity and levels in the serum.

HU-211 and HU-245, when coadministered with LPS, significantly reduced both levels and activity of TNF in the serum of mice.

Determination of TNF Activity: Experimental Procedure

Mice (C57BL/6) were injected ip with 100 µg LPS, concomitantly with HU-211, HU-210, or HU-245 (200 µg/mouse), and 90 min later they were bled, the sera separated and TNF was assayed for its activity (bioassay) and levels (using ELISA kit).

Figure 1A:
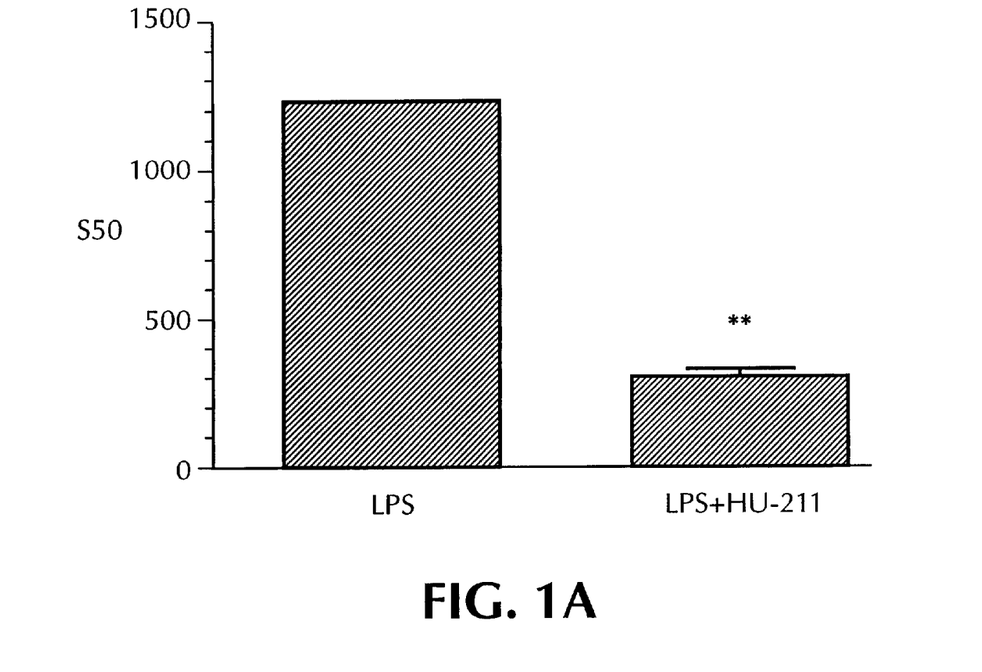
Figure 1B:
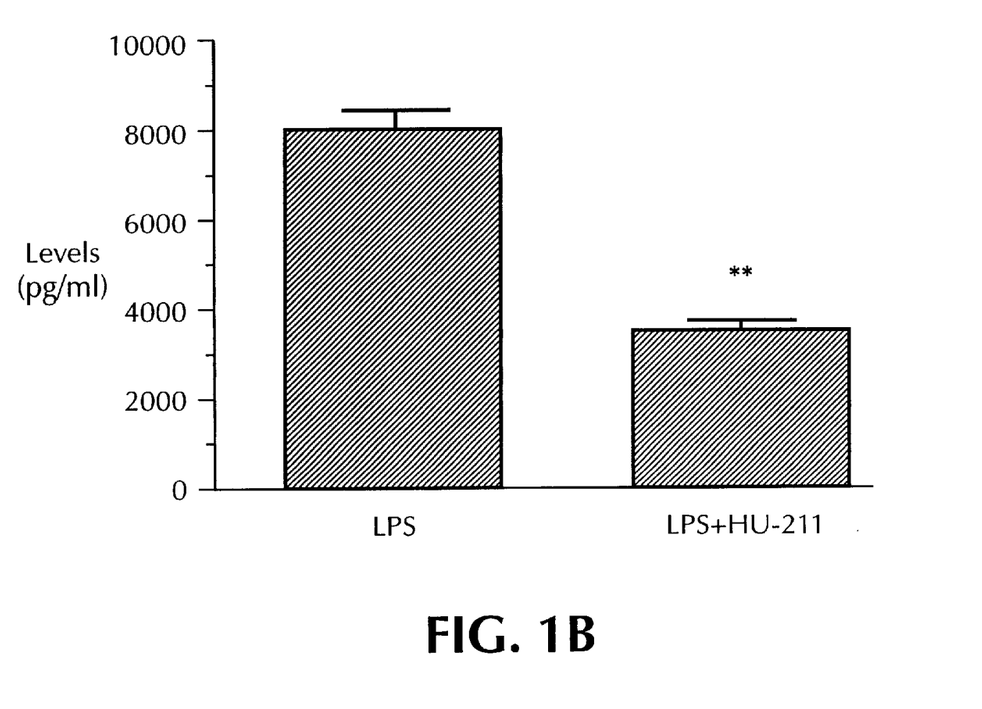

Results:

FIGS. 1 (A&B) depicts the activity (S50) and levels (pg/ml) of TNF in the sera of the LPS treated mice. It is apparent that HU-211 attenuated the LPS-induced production and action of TNF to a very pronounced extent.

HU-245 also showed a pronounced effect on TNF levels, as determined by bioassay. The $S_{50}$ found for animals treated with HU-245 was 44±11 vs. 1233±237 found for control animals treated with LPS alone.

Physiological Example 3
Protective Effect of HU-211 on Survival of LPS Treated Mice The effect of HU-211 on the survival of mice, in response to administration of LPS was assessed. The survival was followed up to 48 hr.

HU-211, administered 30 min prior to LPS, significantly reduced mortality of the mice.

Animals and Materials:
BALB/c male mice 20–25 gr (Anilab, Israel); HU-211 5% in cosolvent, (Pharmos Ltd., Israel, batch no. 4T01HS); Blank cosolvent, (Pharmos batch no. c-00-502002); LPS, *E. Coli* 055:B5, (Difco USA, batch no. 1001007); Saline (Braun, Germany batch no. 3431A41A).

Procedure:
Animals are administered with either HU-211 at a dose of 10 mg/kg i.p. or vehicle alone (10 ml/kg i.p.), and 30 minutes later with LPS IV. Two dose levels of LPS were tested in the present study: 10 and 15 mg/kg.

Figure 2A:
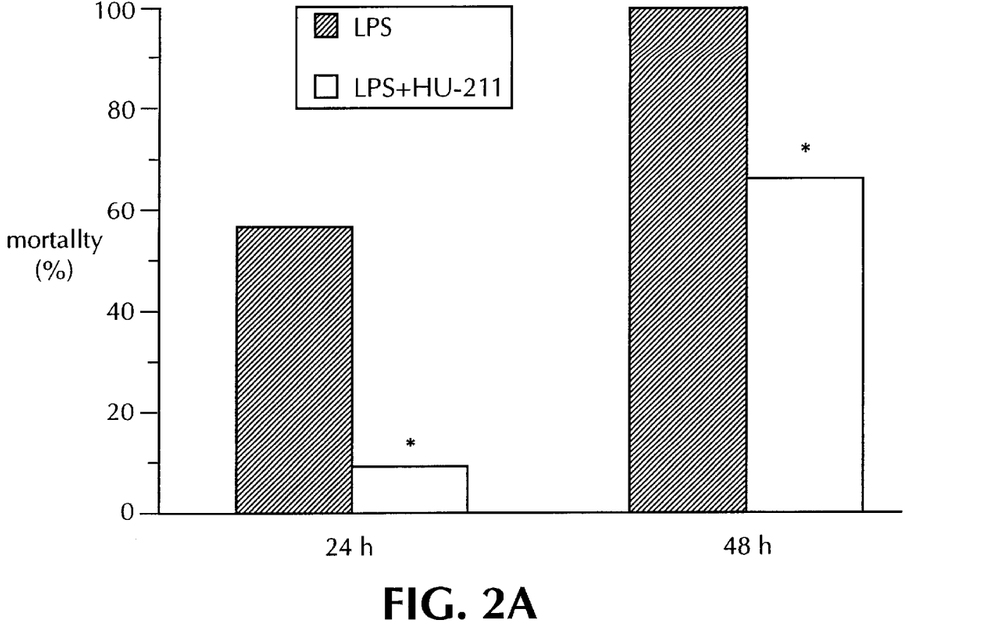

Mortality rate was recorded once a day for 2 days.
Results (FIG. 2a)

LPS 15 mg/kg dose level caused 67% mortality (4/6, survival rate of 33%) 24 hours post vehicle administration. By 48 hours post vehicle administration none of the vehicle treated mice survived.

LPS 15 mg/kg dose level caused 33% mortality (2/6, 67% survival rate) 24 hours post HU-211 administration. By 48 hours post HU-211 administration none of the animals survived. The difference between HU-211 activity and vehicle was not statistically significant, at this dose level.

LPS 10 mg/kg dose level caused 57% mortality (8/14, 43% survival rate) 24 hours post vehicle administration. At 48 hours after vehicle administration none of the animals survived.

The same dose level caused only 9% mortality (1/12, 91% survival rate) 24 hours post HU-211 administration. After 48 hours 4 out of the 12 tested animals survived (33%). None of the animals survived 72 hours post LPS administration. These differences were statistically significant, p<0.02 Fisher exact test for both 24 and 48 hours.

Conclusions
HU-211 at a dose level of 10 mg/kg i.p. administered 30 minutes before LPS administration, induced a statistically significant protection (p<0.02) at both 24 and 48 hrs. after LPS administration.

Physiological Example 4
Protection Against LPS-Induced Hypotension

The purpose of this study was to test the possible effect of HU-211 on the cardiovascular alterations induced by LPS administration.

Animals and Materials:
Male and female Sprague Dawley rats (Harlan, Israel); HU-211 5% in cosolvent, (Pharmos Ltd., Israel, batch no. 4T01HS); Blank cosolvent, (Pharmos batch no. c-00-502002); LPS, *E. Coli* 055:B5, (Difco USA, batch no. L001007); Saline (Braun, Germany batch no. 3431A41A); Halothane anesthetic (Fluthane, Zeneca, U.K. batch no. ML040); Heparin 5000 IU/ml (Chaoy, France batch no. 1842).

Procedure:
Rats were individually anesthetized with halothane in 70% nitrogen, 30% oxygen. The right femoral artery was catheterized using polyethylene tubes (PE-50, Clay Adams, USA), and connected to a computerized physiograph through a pressure transducer (XTT Vigo, USA). The animals are then connected via a rectal probe to the above physiological recorder. Rectal temperature is kept throughout the study between 37° C. and 38° C., using a heating lamp. Following 10–15 minutes of baseline recording, animals are intravenously administered an injection of saline, vehicle alone or HU-211 at a dose of 4 mg/kg. As soon as possible after completion of the first injection (2–5 minutes later) they are administered an intravenous injection of LPS at a dose of 15 mg/kg (in a volume of 3 ml/kg). Blood pressure and heart rate are recorded for the following 4 hrs. The hematocrit is measured and recorded just prior to drug administration, and 1, 2, and 3 hours later. At the end of the follow up period, animals are sacrificed by deep anesthesia with halothane.

Figure 3A:
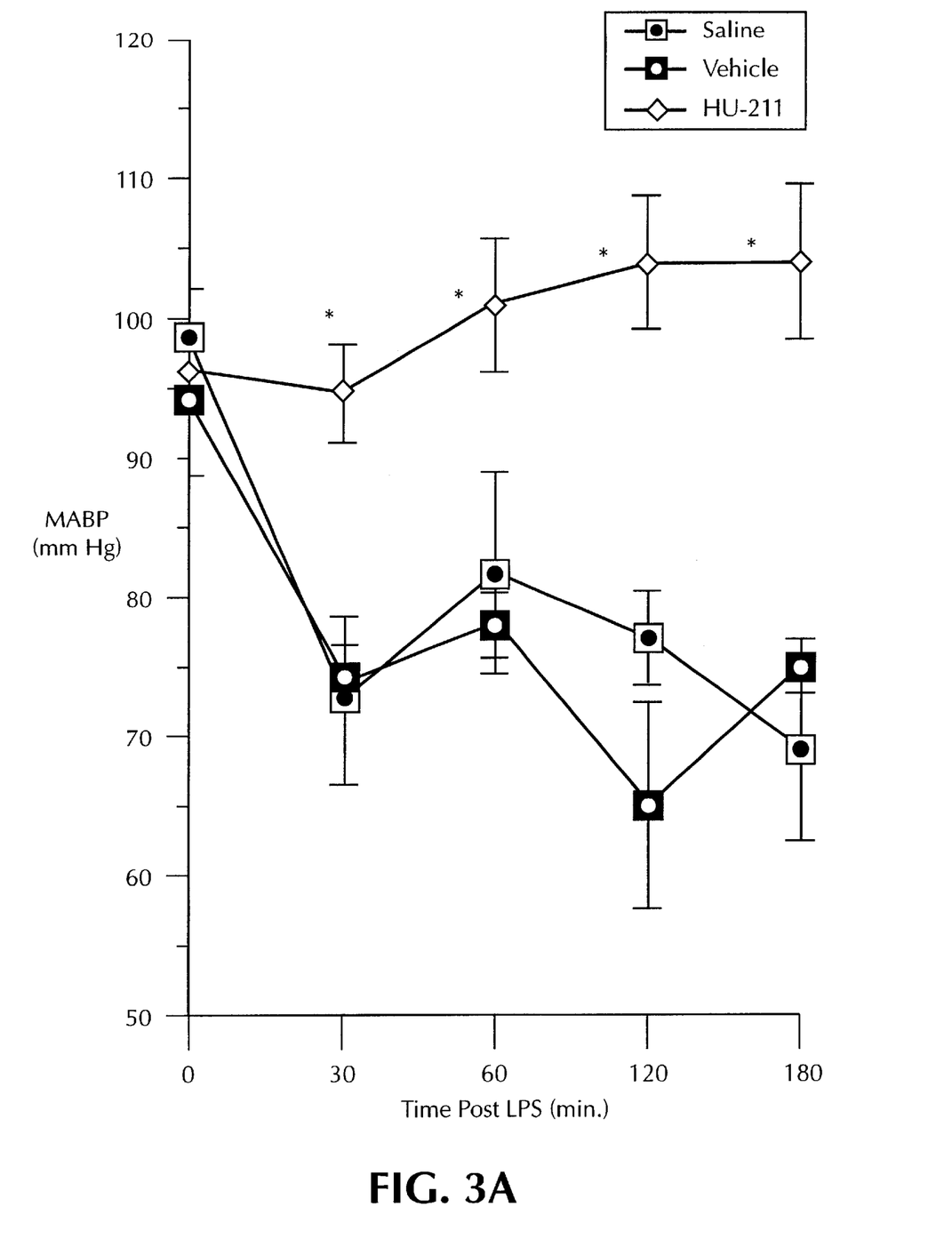
Figure 3B:
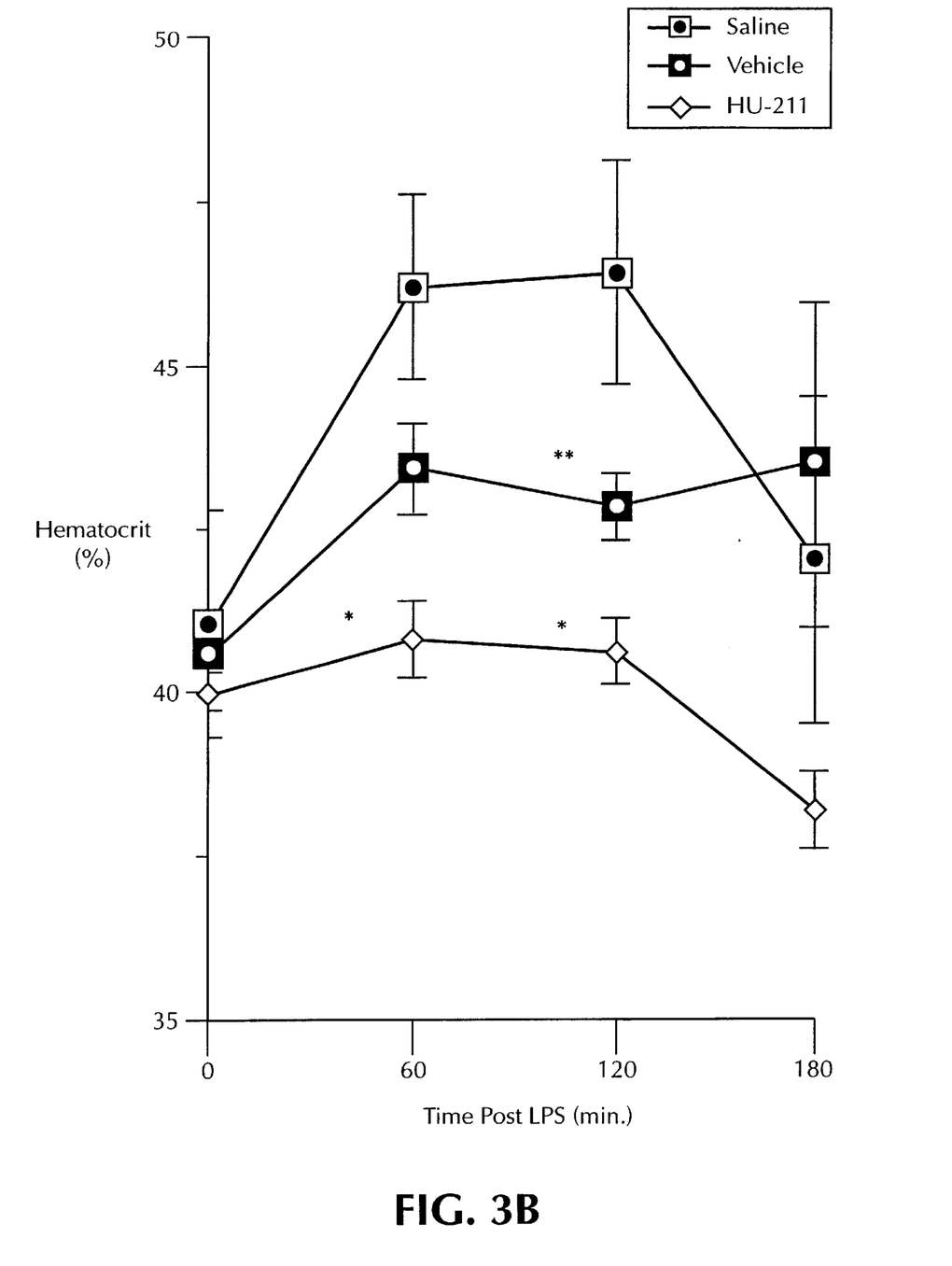

Results
Administration of LPS at a dose of 15 mg/kg to rats caused a reduction of around 30% in mean arterial blood pressure (MABP). This drop in blood pressure was abolished by pre-administration of HU-211 (at a dose of 4 mg/kg) intravenously. A transient hypotension was evident 10 minutes after LPS administration in the HU-211 treated rats. This lasted for 5–10 minutes and by 30 minutes post-LPS administration normotension was regained. The differences in MABP were statistically significant between the HU-211 treated and the control groups (Student's t-test), as shown in FIG. 3a. LPS also induced an increase of about 10% in hematocrit. This increase was prevented by administration of HU-211 at a dose of 44 mg/ml administered intravenously 2–3 minutes before LPS administration (FIG. 3b). These differences were statistically significant 60 and 120 minutes post LPS administration.

Physiological Example 5
Protection Against Septic Shock.

The effect of HU-211 in endotoxic shock was assessed in a model of lethal toxicity by lipopolysacharide (LPS) in D-galactosamine (D-GALN)-sensitized mice (Galanos et al. PNAS 76: 5739, 1979, Lehman et al. J. Exp. Med. 165: 657, 1987). In this model 100% mortality occurs within 6–8 hrs of administration of the combined treatment.

Experimental Procedure:
LPS (10 ng/mouse) and D-GALN (18 $\mu$g/mouse) were coadministered to 20 mice (C57BL/6). Half of the mice served as controls, and the other were treated within 5 min of injection with HU-211 (7.5 mg/kg body weight), followed by 8 additional injections every hour. The survival was followed up to 24 hrs, and the results of this experiment are depicted in Table 1.

TABLE 1

The effect of HU-211 on mice survival after endotoxic shock

| exp. no | lethality in control group: dead/total | lethality in HU-211 treated group dead/total |
|---------|----------------------------------------|----------------------------------------------|
| 1       | 5/5                                    | 1/5                                          |
| 2       | 10/10                                  | 1/10                                         |
| 3       | 5/5                                    | 0/5                                          |
| total:  | 20/20 (0% survival)                    | 2/20 (90% survival)                          |

Figure 2B:
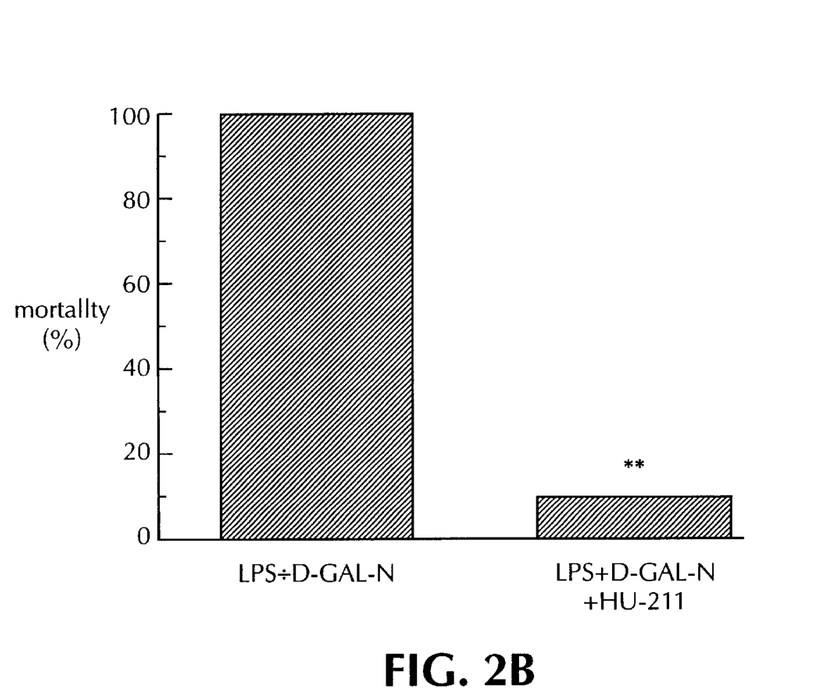

The treatment with HU-211 rescued 90% of the mice (FIG. 2B), with 18 out of 20 HU-211 treated mice surviving the shock, whereas none of the controls (20 mice) survived.

Conclusion:
To date, mortality from septic shock remains very high, despite advances in surgical and medical sciences. The results of our experiment are encouraging and may serve as a basis for saving lives of patients with septic shock.

Physiological Example 6
The Effect of HU-211 on TNF Production in a Rat Model of Head Trauma The effect of HU-211 on TNF production was assessed in a model of head trauma (HT) in rats. Injury was induced in anesthetized rats by a weight-drop device followed by a recovery period of up to 30 days. This type of trauma produces brain edema (i.e. increase in water content, decrease in specific gravity in the brain), breakdown of the blood brain barrier (BBB), clinical and cognitive dysfunction.

HU-211 significantly reduces reduced edema and improved the clinical outcome measured 48 hours after HT (Shohami et al., *J. Neurotrauma* 10: 109, 1993; Brain Res. 674, 55–62, 1995)

Experimental Procedure:

The model was described in detail by Shapira et al., *Crit. Care Med.* 16: 258–265, 1988. Rats were subjected to head trauma (HT) by a weight-drop device and surviving rats were followed up for 30 days post trauma.

Figure 4A:
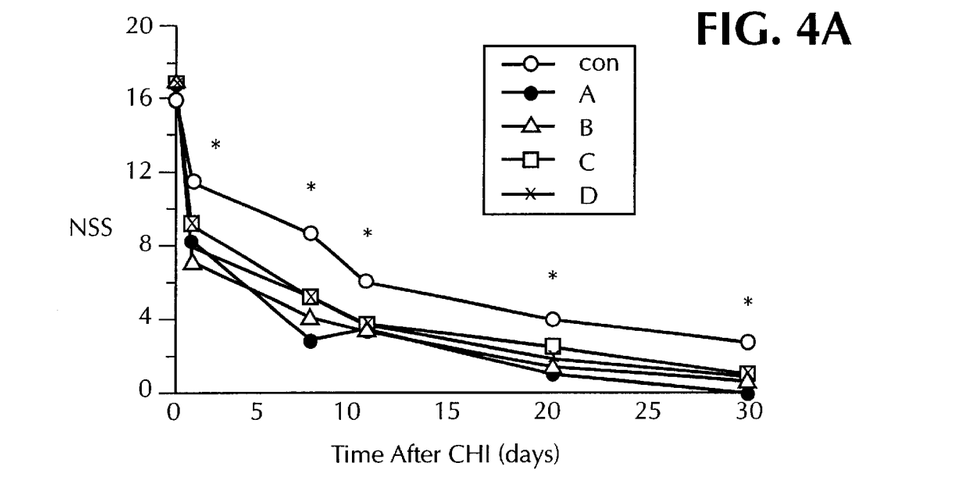

In this experiment we compared the effects of two agents: 1) pentoxyfilline (PTX), a methylxanthine known for its ability to prevent or attenuate the LPS-induced release of TNF both in vitro and in vivo. This effect was found to be exerted at the transcriptional level (Doherty et al., 1991); and 2) HU-211, which was previously shown to have potent cerebroprotective effects in the CHI model (Shohami et al. loc. cit., FIG. 4A). The levels of TNF were measured after CHI in order to determine whether the beneficial effect of HU-211 is also associated with suppression of TNF production or activity.

Results

Figure 4B:
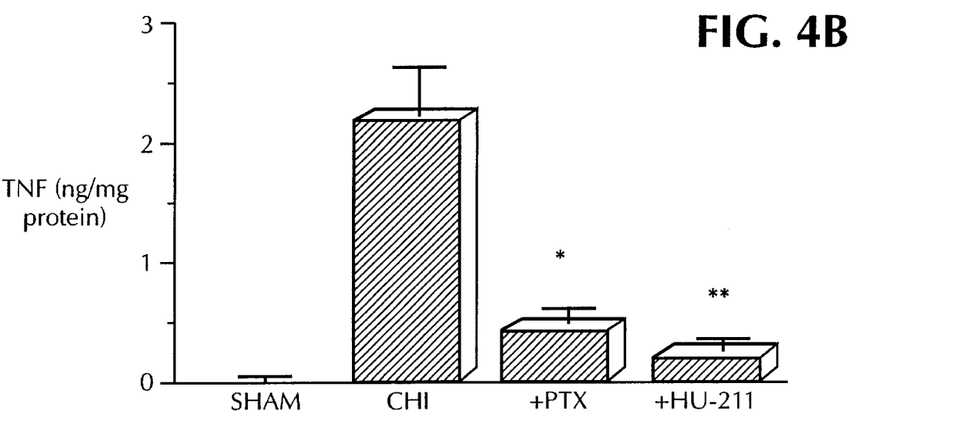
Figure 4C:
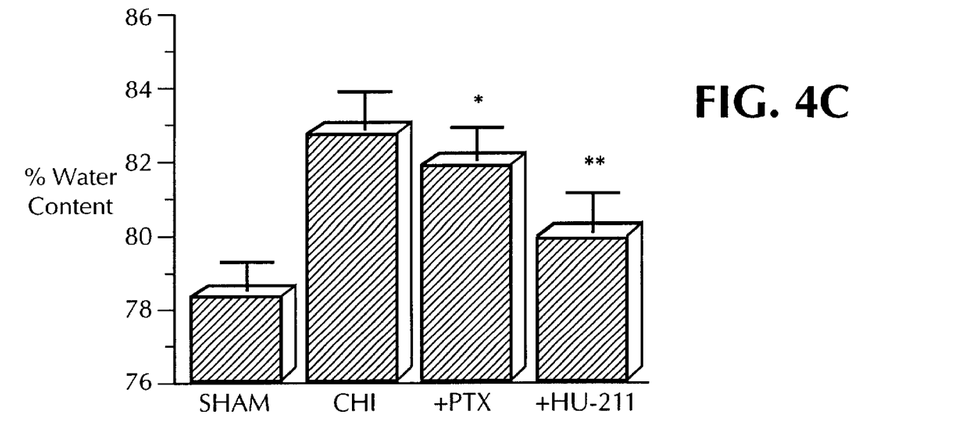

As shown in FIG. 4, the protective effect of HU-211 is significantly superior to that of pentoxyfilline in terms of brain tissue water content (a measure of the anti-edema effect of the compounds) and in terms of the brain levels of TNF after CHI.

Conclusion

Severe head injury, or cerebral ischemia, is associated with a high mortality rate (exceeding 50%) and poor functional outcome. Despite extensive clinical and experimental research, there are no well-defined therapies for these conditions. There are very few available treatments for brain injury today and the gradual progressive biochemical changes which occur after head trauma can lead to the evolution of permanent neuronal damage. The results clearly demonstrate that the compounds of the instant invention, namely HU-211, possess protective properties in a model of closed head injury in rats.

Physiological Example 7
Attenuation of Experimental Autoimmune Arthritis in Mice The purpose of this study is to test the activity of HU-211 vs. arthritis, induced by collagen type 2 incorporated into complete Freund's adjuvant.

Materials and Methods

CD-1 male mice (27–33 gr.), five in each treatment group (supplied by Harlan Israel) were used in the present study. Each animal was administered with collagen type 2 (Sigma, batch no. 111H7180) 100 $\mu$g/ml in 0.1 ml complete Freund's adjuvant (Sigma batch no. 084H8800). The collagen was administered s.c. into the base of the tail. The volume of each hind paw was measured using a plathysmometer (Hugo Basill, Italy) before collagen administration and on days 1, 4, 7, 10, 13 and 16 of treatment (30 minutes after drug treatment).

Five treatment groups were tested in the present study: vehicle (blank cosolvent) 10 ml/kg once daily, HU-211 10 mg/kg every three days, HU-211 20 mg/kg once daily, HU-211 20 mg/kg every 3 days and diclofenac 10 mg/kg (10 ml/kg) every 3 days. All treatments were administered intraperitoneally. HU-211 was used from a 5% preparation in cosolvent (Pharmos batch no. PRN-C-08623041), by diluting with saline (B. Braun batch no. 3431A41A) 1:25. The same procedure was performed with blank cosolvent (Pharmos batch no. 608945). Diclofenac was prepared in Pharmos, batch no. LG-121\70 1 mg/ml. At the same time paws were measured they were clinically evaluated according to the following method (Williams R. O., Proc. Natl. Acad. Sci. USA: 89:9784–9788): 0—normal, 1—slight swelling and erythema, 2—pronounced edematous swelling and 3—joint rigidity. On day fifteen of treatment animals were euthanised with pentobarbital 100 mg/kg i.p. (Pental veterinary, C.T.S. Israel, batch no. 170005). Blood samples were taken for hematocrit and blood levels of HU-211 (in heparinized serum).

Figure 5:
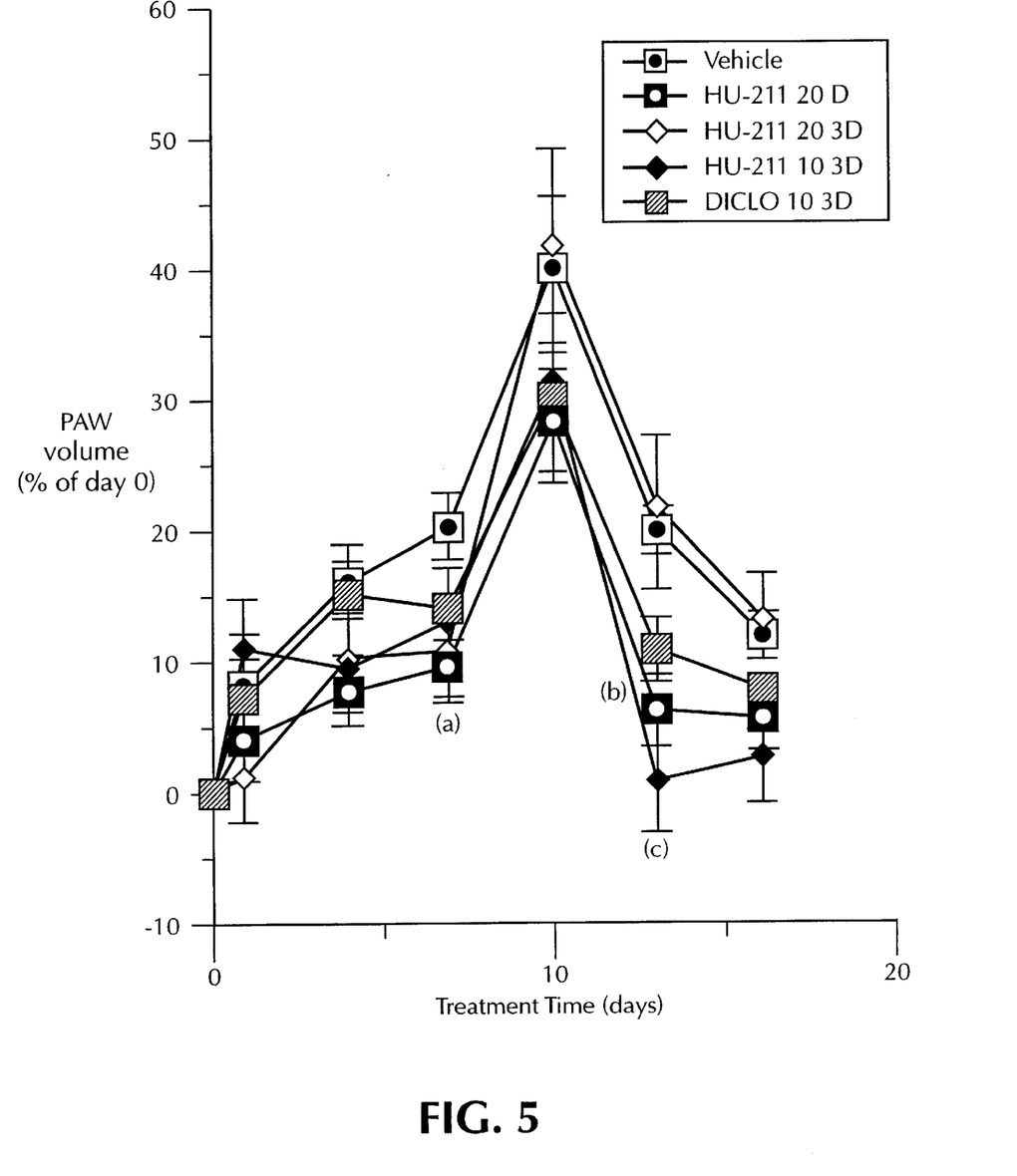
FIG. 5 shows the beneficial effect of HU-211 in collagen induced arthritis in rats.

Results a. Clinical Signs:

The primary arthritis related sign that was evident in the present study was swelling of the paws. Animals treated with HU-211 20 mg/kg (daily or every 3 days) demonstrated the lowest number of these signs, compared to the other treatment groups. These differences were compared using a non parametric analysis (Wilcoxon Rank Sum Test), and were found to be statistical significant ($p<0.01$).

b. Paw Volume (FIG. 5):

All treatments (except the HU-211 20 mg/kg every 3 days) reduced the collagen-induced paw edema by 30–50% compared to the vehicle treated animals (up to 30% increase in paw volume in the treated mice compared to up to 40% increase in the vehicle treated mice). This effect was statistically significant ($p<0.05$) with HU-211 20 mg/kg (daily treatments) and with the HU-211 10 mg/kg every 3 days. The diclofenac treated animals demonstrated a smaller paw volume compared to the vehicle treated rats. But this difference did not reach statistical significance.

Figure 6:
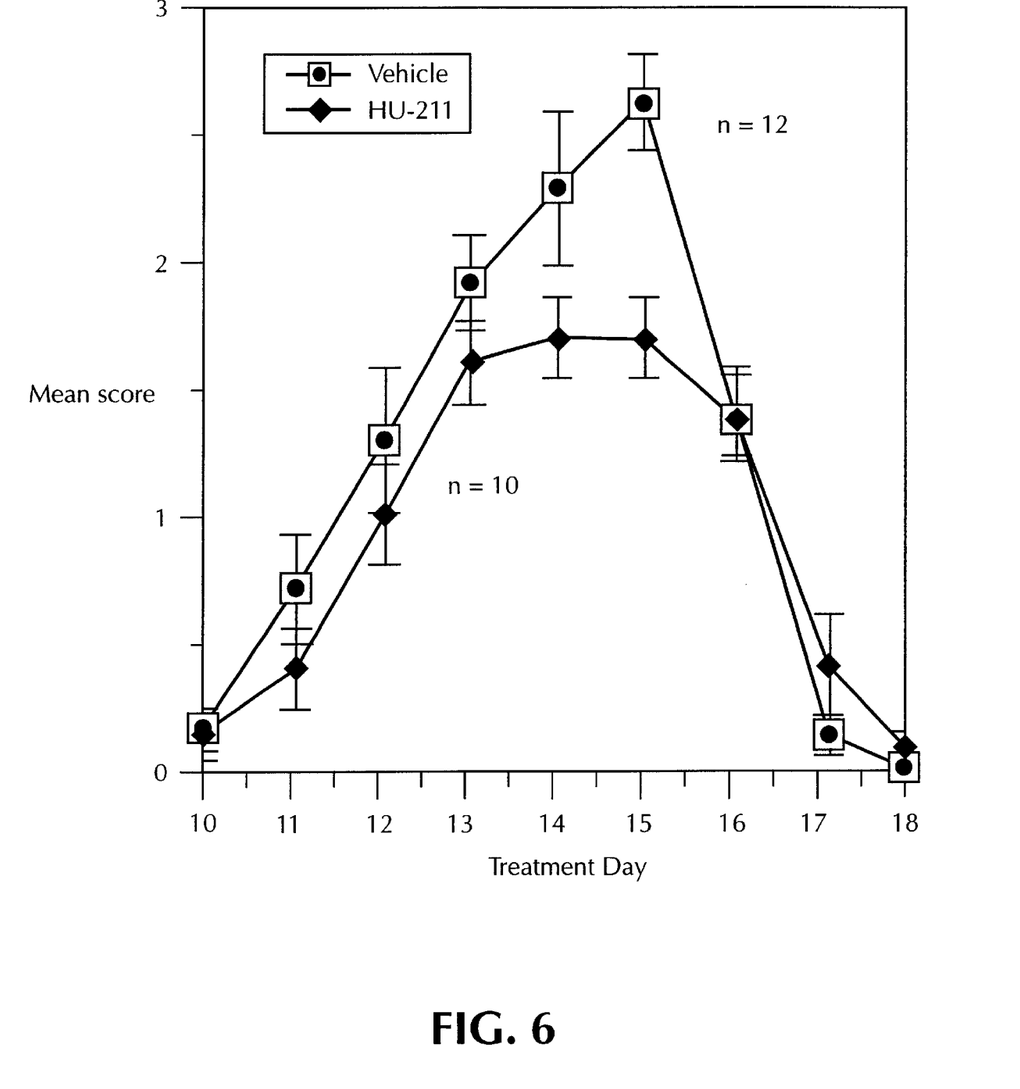
FIG. 6 shows the improved clinical outcome in experimental allergic encephalomyelitis in rats treated with HU-211.

Physiological Example 8
Attenuation of Experimental Autoimmune Encephalomyelitis in Lewis Rats EAE was tested using Lewis rats in which the disease displays onset of symptoms around day 10 after induction and spontaneous recovery around 18 days after induction of the disease. The Lewis rats used were 8 week old females (from OLAC, England). The animals (5 per cage) were maintained on a 12 hour light/12 hour dark regimen, at a constant temperature of 22° C., with food and water ad libitum. EAE was induced in these animals by immunization with purified guinea pig myelin basic protein emulsified in complete Freund's adjuvant. Guinea pig myelin basic protein (mbp) was prepared from spinal cord homogenates defatted with chloroform/ethanol and the isolated protein was purified using ion exchange chromatography. Each animal received 50 micrograms of the purified protein. A solution of mbp (0. 5 mg/ml) was emulsified with an equal volume of Complete Freund's Adjuvant containing 4 mg/ml of mycobacterium tuberculosis, and each animal received 100 microliters (50 $\mu$l in each hind foot pad). Animals were treated with a single injection of HU-211 or vehicle control administered intravenously in a volume of 2 ml. The time of treatment was varied from day 10 to day 18 post induction of disease, with five animals per group. The results of this experiment, which are presented in FIG. 6, show the diminution of mean clinical score in HU-211 treated animals. (Score of 1 indicates tail paralysis, 2 indicates paraplegia, 3 indicates quadriplegia, 4 indicates complete body paralysis and 5 indicates death).

Although the present invention has been described with respect to various specific embodiments thereof in order to illustrate it, such specifically disclosed embodiments should not be considered limiting. Many other specific embodiments will occur to those skilled in the art based upon applicants' disclosure herein, and applicants propose to be bound only by the spirit and scope of their invention as defined in the appended claims.

What is claimed is:

1. A method for treating a patient who exhibits the symptoms associated with cachexia due to acquired immune deficiency syndrome, neoplasia, trauma or other wasting diseases, which method comprises administering to the patient a pharmaceutical composition in order to prevent production of or block the action of tumor necrosis factor in the patient, wherein the pharmaceutical composition comprises a therapeutically effective amount of a compound of the formula (I):

(I)

having the (3S,4S) configuration and being essentially free of the (3R,4R) enantiomer, wherein A - - - B indicates an optional 1(2) or 6(1) double bond,
R is
  (a) —Q wherein Q is a heterocyclic moiety having a labile hydrogen atom so that said moiety acts as a carboxylic acid analogue,
  (b) —R'X wherein R' is $C_1$–$C_5$ alkyl and X is halogen, —OR'' wherein R'' is hydrogen, $C_1$–$C_5$ alkyl, or —OC(O)R''' wherein R''' is hydrogen or $C_1$–$C_5$ alkyl,
  (c) —R'N(R'')$_2$ wherein R' is $C_1$–$C_5$ alkyl and each R'', which may be the same or different, is hydrogen or $C_1$–$C_5$ alkyl optionally containing a terminal —OR''' or —OC(O)R''' moiety wherein R''' is hydrogen or $C_1$–$C_5$ alkyl,
  (d) —R' wherein R' is $C_1$–$C_5$ alkyl,
  (e) —R'OR''' wherein R' is $C_1$–$C_5$ alkyl and R''' is hydrogen or $C_1$–$C_5$ alkyl, or,
  (f) —R'—C(O)—OR''', wherein R' may be absent and R' and R''' are as defined above;
G is
  (a) halogen,
  (b) $C_1$–$C_5$ alkyl, or
  (c) —OR$_1$ wherein R$_1$ is
    (a') —R'', wherein R'' is hydrogen or $C_1$–$C_5$ alkyl optionally containing a terminal —OR''' or —OC(O)R''' moiety wherein R''' is hydrogen or $C_1$–$C_5$ alkyl, or
    (b') —C(O)R''' wherein R''' is as previously defined; and
R$_2$ is
  (a) $C_1$–$C_{12}$ alkyl,
  (b) —OR'''', in which R'''' is a straight chain or branched $C_2$–$C_9$ alkyl which may be substituted at the terminal carbon atom by a phenyl group, or
  (c) —(CH$_2$)$_n$OR''' wherein n is an integer of 1 to 7 and R''' is hydrogen or $C_1$–$C_5$ alkyl.

2. The method of claim 1 wherein A - - - B designates a 1(2) or 6(1) double bond, R is lower alkyl of 1–3 carbon atoms or CH$_2$OH, G is hydroxy or a lower acyloxy group, and R$^2$ is (a) a straight or branched $C_6$–$C_{12}$ alkyl radical or (b) a group OR$^3$ in which R$^3$ is a straight or branched $C_5$–$C_9$ alkyl radical optionally substituted at the terminal carbon atom by a phenyl group.

3. The method of claim 1 wherein A - - - B designates a 1(2) or 6(1) double bond, R is COOR''' wherein R''' is lower alkyl of 1–5 carbon atoms or hydrogen, G is hydroxy or a lower acyloxy group, and R$^2$ is (a) a straight or branched $C_6$–$C_{12}$ alkyl radical or (b) a group OR$^3$ in which R$^3$ is a straight or branched $C_5$–$C_9$ alkyl radical optionally substituted at the terminal carbon atom by a phenyl group.

4. The method of claim 1 in which said pharmaceutical composition includes a carrier or diluent.

5. The method of claim 4 which comprises selecting the carrier or diluent to be an aqueous cosolvent solution comprising a pharmaceutically acceptable cosolvent, a micellar solution prepared with natural or synthetic ionic or non-ionic surfactants, or a combination of such cosolvent and micellar solutions.

6. The method of claim 4 which comprises selecting the carrier to be a solution of ethanol, a surfactant, and water.

7. The method of claim 4 which comprises selecting the carrier to be an emulsion comprising a triglycerides, lecithin, glycerol, an emulsifier, an antioxidant, and water.

8. A method according to claim 4, wherein the daily dosage of said compound is between 0.1 and 25 mg/kg.

9. A method according to claim 4, in which said pharmaceutical composition is administered intravenously, intrathecally, orally or by inhalation.

10. A method for treating a patient who exhibits the symptoms associated with autoimmune diseases characterized by the production of elevated levels of tumor necrosis factor, which method comprises administering to the patient a pharmaceutical composition in order to prevent production of or block the action of tumor necrosis factor in the patient, wherein the pharmaceutical composition comprises a therapeutically effective amount of a compound of the formula (I):

(I)

having the (3S,4S) configuration and being essentially free of the (3R,4R) enantiomer, wherein A - - - B indicates an optional 1(2) or 6(1) double bond,
R is
  (a) —Q wherein Q is a heterocyclic moiety having a labile hydrogen atom so that said moiety acts as a carboxylic acid analogue,
  (b) —R'X wherein R' is $C_1$–$C_5$ alkyl and X is halogen, —OR'' wherein R'' is hydrogen, $C_1$–$C_5$ alkyl, or —OC(O)R''' wherein R''' is hydrogen or $C_1$–$C_5$ alkyl,
  (c) —R'N(R'')$_2$ wherein R' is $C_1$–$C_5$ alkyl and each R'', which may be the same or different, is hydrogen or $C_1$–$C_5$ alkyl optionally containing a terminal —OR''' or —OC(O)R''' moiety wherein R''' is hydrogen or $C_1$–$C_5$ alkyl,
(d) —R' wherein R' is $C_1$–$C_5$ alkyl,
(e) —R'OR''' wherein R' is $C_1$–$C_5$ alkyl and R''' is hydrogen or $C_1$–$C_5$ alkyl, or,
(f) —R'—C(O)—OR''', wherein R' may be absent and R' and R''' are as defined above;

G is
(a) halogen,
(b) $C_1$–$C_5$ alkyl, or
(c) —$OR_1$ wherein $R_1$ is
(a') —R'', wherein R'' is hydrogen or $C_1$–$C_5$ alkyl optionally containing a terminal —OR''' or —OC(O)R''' moiety wherein R''' is hydrogen or $C_1$–$C_5$ alkyl, or
(b') —C(O)R''' wherein R''' is as previously defined; and $R_2$ is
(a) $C_1$–$C_{12}$ alkyl,
(b) —OR'''', in which R'''' is a straight chain or branched $C_2$–$C_9$ alkyl which may be substituted at the terminal carbon atom by a phenyl group, or
(c) —$(CH_2)_n$OR''' wherein n is an integer of 1 to 7 and R''' is hydrogen or $C_1$–$C_5$ alkyl.

11. The method of claim 10 wherein A - - - B designates a 1(2) or 6(1) double bond, R is lower alkyl of 1–3 carbon atoms or $CH_2OH$, G is hydroxy or a lower acyloxy group, and $R^2$ is (a) a straight or branched $C_6$–$C_{12}$ alkyl radical or (b) a group $OR^3$ in which $R^3$ is a straight or branched $C_5$–$C_9$ alkyl radical optionally substituted at the terminal carbon atom by a phenyl group.

12. The method of claim 10 wherein A - - - B designates a 1(2) or 6(1) double bond, R is COOR''' wherein R''' is lower alkyl of 1–5 carbon atoms or hydrogen, G is hydroxy or a lower acyloxy group, and $R^2$ is (a) a straight or branched $C_6$–$C_{12}$ alkyl radical or (b) a group $OR^3$ in which $R^3$ is a straight or branched $C_5$–$C_9$ alkyl radical optionally substituted at the terminal carbon atom by a phenyl group.

13. The method of claim 10 in which said pharmaceutical composition includes a carrier or diluent.

14. The method of claim 10 which comprises selecting the carrier or diluent to be an aqueous cosolvent solution comprising a pharmaceutically acceptable cosolvent, a micellar solution prepared with natural or synthetic ionic or non-ionic surfactants, or a combination of such cosolvent and micellar solutions.

15. The method of claim 10 which comprises selecting the carrier to be a solution of ethanol, a surfactant, and water.

16. The method of claim 10 which comprises selecting the carrier to be an emulsion comprising a triglycerides, lecithin, glycerol, an emulsifier, an antioxidant, and water.

17. A method according to claim 10, wherein the daily dosage of said compound is between 0.1 and 25 mg/kg.

18. A method according to claim 10, in which said pharmaceutical composition is administered intravenously, intrathecally, orally or by inhalation.

* * * * *

UNITED STATES PATENT AND TRADEMARK OFFICE
CERTIFICATE OF CORRECTION

PATENT NO.    : 6,545,041 B2
DATED         : April 8, 2003
INVENTOR(S)   : Shohami et al.

It is certified that error appears in the above-identified patent and that said Letters Patent is hereby corrected as shown below:

<u>Title page,</u>
Item [73], Assignee, change "Yessum" to -- Yissum --.

Signed and Sealed this

Fifth Day of August, 2003

JAMES E. ROGAN
*Director of the United States Patent and Trademark Office*